(12) United States Patent
Beger et al.

(10) Patent No.: US 9,421,040 B2
(45) Date of Patent: Aug. 23, 2016

(54) SYSTEM FOR ANCHORING A PEDICLE SCREW, ASSOCIATED KIT, SPACER AND PEDICLE AUGMENTATION

(71) Applicant: Aesculap AG, Tuttlingen (DE)

(72) Inventors: Jens Beger, Tuttlingen (DE); Susanne Klingseis, Biberach (DE)

(73) Assignee: Aesculap AG (DE)

( * ) Notice: Subject to any disclaimer, the term of this patent is extended or adjusted under 35 U.S.C. 154(b) by 70 days.

(21) Appl. No.: 14/336,382

(22) Filed: Jul. 21, 2014

(65) Prior Publication Data
US 2015/0032159 A1  Jan. 29, 2015

(30) Foreign Application Priority Data

Jul. 23, 2013  (DE) .................. 10 2013 107 881

(51) Int. Cl.
*A61B 17/70* (2006.01)
*A61B 17/86* (2006.01)
(Continued)

(52) U.S. Cl.
CPC ......... *A61B 17/7032* (2013.01); *A61B 17/686* (2013.01); *A61B 17/7059* (2013.01); *A61B 17/8061* (2013.01); *A61B 17/863* (2013.01); *A61B 17/864* (2013.01); *A61B 17/8605* (2013.01); *A61L 31/06* (2013.01);
(Continued)

(58) Field of Classification Search
CPC ............ A61B 17/8605; A61B 17/863; A61B 17/864; A61B 17/868; A61B 17/7032; A61B 17/8061; A61B 31/06; A61B 31/088; A61B 31/146; C08L 71/12; A61L 2430/38

USPC .................. 606/246–279, 300–308
See application file for complete search history.

(56) References Cited

U.S. PATENT DOCUMENTS 7,918,853 B2 * 4/2011 Watanabe ............ A61B 17/164
606/62
7,935,138 B1  5/2011 Richelsoph
(Continued)

FOREIGN PATENT DOCUMENTS

DE 602004012579 T2  4/2009
EP    1661527 A1  5/2006
(Continued)

OTHER PUBLICATIONS

European Search Report with English Translation issued in related European Application No. 14177888.6, dated Dec. 18, 2014.
(Continued)

*Primary Examiner* — Pedro Philogene
(74) *Attorney, Agent, or Firm* — RatnerPrestia (57) ABSTRACT

A system for anchoring a pedicle screw in a patient's vertebra uses a pedicle screw having a threaded portion sinkable in the vertebral arch. The space between the threaded portion and cortical edge layer of the pedicle is at least partially filled by a spacer that enables an all-round support of the threaded portion at the cortical edge layer. A kit includes a pedicle screw and a spacer which at least partially fills the space between the threaded portion and cortical edge layer of the pedicle. A spacer has an essentially oval cross-section for form-locking fit in a corresponding axial recess sunk in the pedicle and having an axial through-hole to accommodate the threaded portion of a pedicle screw, as well as a spacer in the form of an essentially cylindrical pedicle augmentation in the form of a bone screw or a bone bracket.

13 Claims, 6 Drawing Sheets

(51) Int. Cl.
*A61B 17/68* (2006.01)
*A61B 17/80* (2006.01)
*A61L 31/06* (2006.01)
*A61L 31/08* (2006.01)
*A61L 31/14* (2006.01)

(52) U.S. Cl.
CPC ........... *A61L 31/088* (2013.01); *A61L 31/146* (2013.01); *A61L 2430/38* (2013.01)

(56) References Cited

U.S. PATENT DOCUMENTS

| | | |
|---|---|---|
| 8,343,200 B2 | 1/2013 | Khanna |
| 8,388,660 B1 | 3/2013 | Abdou |
| 2008/0086131 A1 | 4/2008 | Daly |
| 2008/0221623 A1* | 9/2008 | Gooch ................. A61B 17/686 606/302 |
| 2010/0016905 A1 | 1/2010 | Greenhalgh |
| 2010/0145463 A1 | 6/2010 | Michelson |
| 2011/0087296 A1 | 4/2011 | Reiley et al. |
| 2011/0144766 A1 | 6/2011 | Kale |
| 2011/0208252 A1* | 8/2011 | Erhart ................. A61B 17/1735 606/310 |
| 2012/0116465 A1 | 5/2012 | Elahinia |
| 2012/0271309 A1 | 10/2012 | Watanabe et al. |
| 2013/0035724 A1* | 2/2013 | Fitzpatrick ........... A61B 17/686 606/272 |

FOREIGN PATENT DOCUMENTS

WO  WO 2008/129241 A1  10/2008
WO  WO 2010/019979 A1  2/2010

OTHER PUBLICATIONS

German Search Report with partial translation issued in related German Application No. 10 2013 107 881.8, dated Mar. 26, 2014.

* cited by examiner

SYSTEM FOR ANCHORING A PEDICLE SCREW, ASSOCIATED KIT, SPACER AND PEDICLE AUGMENTATION

RELATED APPLICATIONS

This application claims the benefit of priority of German Application No. DE 10 2013 107 881.8, filed Jul. 23, 2013, the contents of which is incorporated by reference herein in its entirety.

FIELD

The invention relates to a system for anchoring a pedicle screw in a vertebra of a patient, in particular in the lumbar or thoracic region of the spinal column.

BACKGROUND

In such systems a bone screw, such as for example a pedicle screw, is screwed into the vertebral arch and into the pedicle adjoining it, wherein the anchoring is controlled via a particular design of the pedicle screw thread and/or of the core cross section of the pedicle screw.

Pedicle screws are used chiefly for posterior thoraco-lumbar stabilization systems, whereby a fixation of the spine is sought with a screw-rod system. The pedicle screws used here are exposed to considerable stress, such that a very great variety of approaches have been disclosed with which the anchoring in the pedicle channel is meant to be improved.

Thus for example an arrangement is known from document U.S. Pat. No. 8,388,660 B1, whereby a screw shaft extends through a threaded sleeve which is expanded outward for anchoring in the pedicle in the transition to the vertebral body.

In document US 2012/0116465 A1 a screw is also used, which has a radially expandable distal threaded portion.

According to U.S. Pat. No. 8,343,200 B2 a pedicle screw is used which is screwed into a screw sleeve. According to U.S. Pat. No. 7,935,138 B1 the outer screw sleeve, in a similar construction, is executed in slotted fashion.

Finally a system is known from document US 2008/0086131 A1 whereby the additional fixing of the pedicle screw occurs by means of a ring lying beneath the screw head, which embeds itself with thorn-like extensions into the vertebral arch.

All known solutions have either the disadvantage that the radial expanding occurs with little control, whereby an increased risk of fracture results, or otherwise the disadvantage (in the case of using the spikes according to US 2008/0086131 A1) a more or less uncontrolled influence on the bone substance which may lead to bone damage.

SUMMARY

The invention is based on the object of providing a system for anchoring a pedicle screw in a vertebra of a patient, an associated kit for this system, and the components required for it, with which it is possible to increase the anchoring stability while protecting the bone substance as much as possible.

According to the invention, the path of a pedicle augmentation is taken to achieve an all-round support of the pedicle screw at the so-called corticalis, that means at the cortical edge layer of the vertebral arch including the vertebral arch root (pedicle). The invention is based on the following considerations:

The pedicle of a lumbar and thoracic vertebra describes approximately an oval structure which is formed by the outer cortical layer of the so-called compact bone, and a spongy inner structure of the so-called cancellous bone. Usually a cylindrical pedicle screw can support itself only at two sides of the pedicle wall. In principle, it is possible to position the screw as cranially or caudally as possible, whereby a further support point can be provided. Thereby however the problem is still not solved of reliably receiving the transverse forces in the cranio-caudal direction and the bending moments occurring in this plane, such that a so-called "windshield wiper effect", that means a loosening of the pedicle screw, does not occur.

According to the invention by contrast a spacer filling at least in regions the space between the threaded portion and cortical edge layer of the pedicle, wherein the spacer is configured or positioned with respect to the threaded portion in the pedicle cross section such that an all-round support of the threaded portion of the pedicle screw at the cortical edge layer via the spacer—a plurality of spacers may also be used—is enabled. This all-round support permits the above-mentioned transverse forces in the cranio-caudal direction and the bending moment acting on the pedicle screws during spinal fixation to be significantly more securely received, compared to the case with conventional systems, which leads to a significant improvement of the surgical technique.

The implementation of the pedicle augmentation may be performed in different ways.

According to a first variant, a cylindrical body filling the pedicle cross section up to the cortical edge layer is used, which sits with form-locking fit in a corresponding axial recess of the pedicle, said axial recess being sunk in the pedicle, and has an axial through-hole for the accommodation of the threaded portion of the associated pedicle screw. The outer circumferential surface of the spacer configured in this way can thereby be additionally engaged with the complementary inner surface of the recess in the pedicle, by means of toothing, for example by means of micro-serrations. Since the cylindrical body fills the pedicle cross section up to the cortical edge layer, it has a cross-section deviating from the circular shape, such that a rotational fixing in the vertebra is provided by the cylindrical shape alone. When the pedicle screw is screwed into the spacer, the threaded portion of the pedicle screw can support itself on all sides at the cortical edge layer of the pedicle and thereby in particular significantly improve the flexural strength of the anchoring in the cranio-caudal plane.

A particularly simple form for the spacer features an oval cross-sectional shape. The oval cross-sectional shape approaches the anatomy or the pedicle geometry and pedicle structure, wherein the particular advantage results that no edge is present in the region of the joining surfaces between spacer and axial recess in the pedicle, which could lead to stress concentrations.

For the preparation, the pedicle may be either drilled or milled, wherein preferably in this case a drilling jig or other tool template is used. Alternatively a preparation with help of an ultrasound osteotome is also possible.

The spacer itself may be made of different materials. A particularly economical, yet sufficiently solid construction is obtained when the spacer is made from plastic, such as for example an organic polymer thermoplastic from the material group of polyetherketones such as PEEK (polyetheretherketone). Advantageously this PEEK plastic may be provided with a porous titanium coating which is used by the Applicant Aesculap AG under the designation "Plasmapore". However for the material for the spacer, one may also select materials from the group of titanium or titanium alloy, synthetic bone substitutes, allogenic bone material, collagen, pressed textile material or any other lattice structure material.

Another variant for the realizing of the spacer filling the space between the threaded portion of the pedicle screw and the cortical edge layer of the pedicle includes at least one spacer formed from an essentially cylindrical pedicle augmentation axially parallel to the pedicle screw inserted in the vertebra, which pedicle augmentation has essentially the shape of a bone screw or a bone dowel and has a cylindrical recess on the side facing the pedicle screw on which the threaded portion supports itself with radial clamping.

The pedicle augmentation according to the invention, which cooperates with the pedicle screw in single or multiple execution, fills the pedicle space remaining between the pedicle screw and the corticalis in an orientation axially parallel to the pedicle screw such that the threaded portion supports itself on the one side directly on a plurality of points and on the other side via the pedicle augmentation over a plurality of points all around at the corticalis of the pedicle. The aforementioned increase of the bending support moment provided by the anchoring of the pedicle screw is in this way optimally ensured, without having to raise the risk of bone fractures or bone damage.

In embodiments where the threaded portion supports itself at the pedicle augmentation with axial clamping, the pedicle screw is even better braced in the pedicle, not only transversely to the pedicle but also in the longitudinal direction.

In order to fix the axially parallel orientation between pedicle screw and pedicle augmentation not only during the assembly but also in the deployed state, the at least one pedicle augmentation and the pedicle screw extend through a common connection plate in which corresponding axial breakthroughs are configured for the form-locking accommodation of a head section of the pedicle augmentation and a guide portion of the pedicle screw, said guide portion lying beneath the screw head. The further function may thereby be advantageously transferred to the connection plate of providing the pedicle screw with an additional guide during screwing-in, in order to thus improve the positioning accuracy of the pedicle screw. Advantageously the pedicle augmentation, in cooperation with the connection plate, comprises a configuration such that in the augmentation's screwed state an axial locking between connection plate and pedicle augmentation is provided. In this way the connection plate can also be axially positioned via the pedicle augmentation, for example held in firm contact with the bony structure, whereby at the same time the load-bearing capacity of the implant is further increased.

In a particularly simple configuration the axial breakthroughs are formed from circular-cylindrical intersecting breakthroughs, for example from circular-cylindrical holes.

Where the connection plate serves for the axial fixing of the pedicle augmentation and optionally as an axial stop for the pedicle screw, it is possible to provide a defined and spacially fixed stop position of the pedicle screw via the connection plate.

A particularly simple axial securing between a connection plate and pedicle augmentation is achieved where the axial breakthrough for the pedicle augmentation bears, on the side facing away from the breakthrough for the pedicle screw, a securing projection which is receivable with form-locking fit in an annular segment groove of the head section of the pedicle augmentation. By means of this development the assembly of the pedicle augmentation together with the connection plate is particularly simple.

A further possibility, which is very simple from an assembly standpoint, of the axial fixing by the pedicle augmentation and connection plate is achieved where the at least one pedicle augmentation is caulkable with the connection plate.

The force flow between pedicle augmentation and pedicle screw can be additionally optimized where the cylindrical recess in the pedicle augmentation is provided with a thread which can be brought into operative engagement with the threaded portion of the pedicle screw. By means of the design of the thread engagement between the thread in the pedicle augmentation and the threaded portion of the pedicle screw, influence may be made on the radial and/or axial clamping of both components. In addition, it is for example possible to stabilize the axially parallel orientation of pedicle screw and pedicle augmentation over the entire length of the axially parallel extent by having a thread in the pedicle augmentation that is undercut, resulting in an improvement of the assembly state and of the implantation secureness.

The subject of the invention is furthermore a kit for a system for the anchoring of a pedicle screw in a vertebra of a patient, wherein this kit consists of a pedicle screw for example a standard pedicle screw and a spacer having features described herein. In addition the kit may comprise a connection plate having features described herein.

Finally, a separate subject of the present invention, for which separate protection is also claimed, is a spacer for a system for anchoring a pedicle screw in a vertebra of a patient, in the form of a cylindrical body having an essentially oval cross-section for the form-locking fit in a corresponding axial recess of the pedicle, said axial recess being sunk in the pedicle, and having an axial through-hole for the accommodation of the threaded portion of a pedicle screw. The spacer can be composed of plastic including PEEK plastic and preferably comprises a porous titanium coating. The spacer can also be formed from a material from the group of titanium or titanium alloy, synthetic bone substitutes, allogenic bone material, collagen, pressed textile material or any lattice structure material. The spacer can be in the form of an essentially cylindrical pedicle augmentation which has essentially the shape of a bone screw or a bone dowel and has a cylindrical recess on one side for the radial support of a threaded portion of a pedicle screw. The spacer can also have a circular-cylindrical head section in which an annular segment groove for receiving an axially acting locking part is configured. Moreover, the spacer can have a head section on which formed tongues for the caulking with an assembly part are configured. Furthermore, the spacer can have a cylindrical recess provided with a preferably undercut thread for the cooperation with a threaded portion of a pedicle screw.

BRIEF DESCRIPTION OF THE DRAWING FIGURES

Several embodiments of the invention are explained in detail below with reference to the drawing figures, of which.

DETAILED DESCRIPTION

Figure 1:
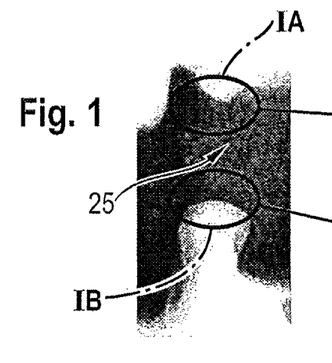
FIG. 1 shows in sections an X-ray photograph of a root of the vertebral arch (of a pedicle)
Figure 1A:
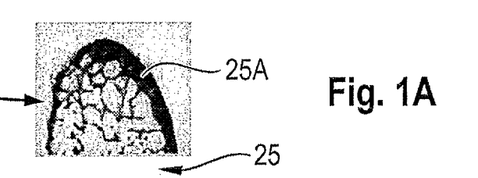
FIG. 1A shows the detail IA in FIG. 1 of a computed tomography representation of the cross-section in this area.
Figure 1B:
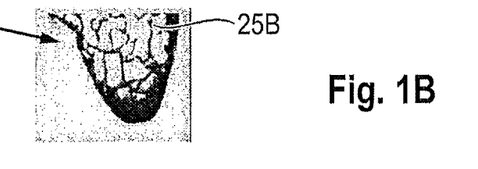
FIG. 1B shows the computed tomography representation of the detail IB in FIG. 1 in cross-section.

The X-ray image according to FIG. 1 and the enlarged computed tomography images of the details IA and IB according to FIG. 1A and FIG. 1B make it clear that the pedicle (indicated with the reference sign 25) of a lumbar and thoracic vertebra has an approximately oval cross-sectional shape. FIGS. 1A and 1B also show that the pedicle 25 has an outer hard bone layer 25A which surrounds an internally lying spongy bone substance called the cancellous bone 25B. This inter-relationship is also apparent from the illustration according to FIG. 4 which illustrates a section of the pedicle perpendicular to its extension.

Figure 4:
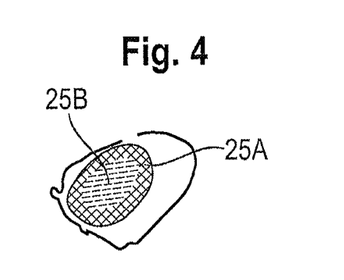
FIG. 4 shows the view of the section according to IV-IV in FIG. 2.

The illustrations of FIGS. 1 and 4 indicate further that the oval cross-section is laid such that the longer extension lies in the cranio-caudal direction.

Figure 2:
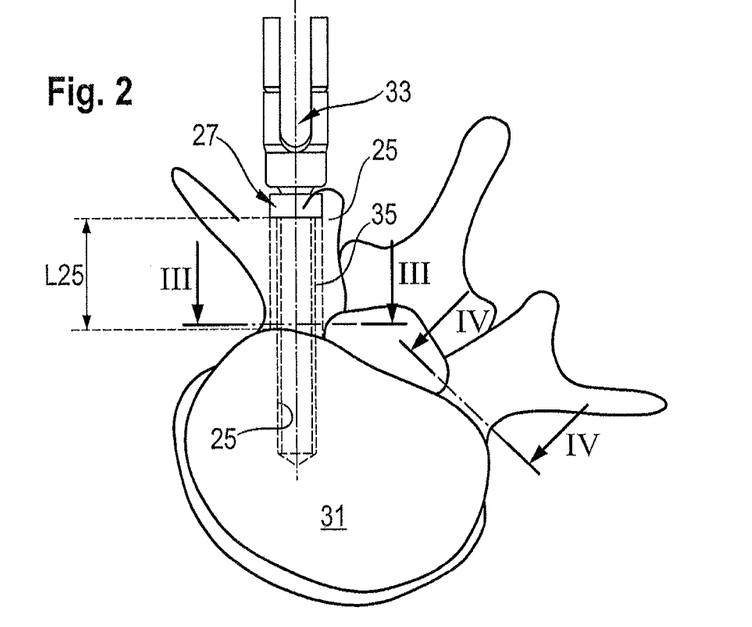
FIG. 2 shows the top view on a vertebra with pedicle screw mounted on one side.

In spinal column surgery a thoraco-lumbar spinal column fixator is often required, with which selected vertebral joints are thereby passivated, such that screwed-in pedicle screws are fixed into their relative positions with respect to each other in the configuration as monoaxial or polyaxial screws with the aid of fixation rods. FIG. 2 shows the top view of a vertebra having a pedicle screw 27 screwed in on one side which extends with its threaded portion 29 through the pedicle 25 up to within the vertebral body 31. The so-called "tulip" of the pedicle screw 27 is indicated with the reference sign 33, in which the fixation rod (not shown in detail) is fixed, wherein by means of the fixing the joint between tulip 33 and the, for example spherical, pedicle screw head is simultaneously locked.

In order to support the threaded portion 29 of the pedicle screw 27 all around the cortical edge layer 25A, the space between the threaded portion 29 and the cortical edge layer 25A of the pedicle 25 is filled by a spacer 35 which is formed in the shown embodiment from a cylindrical body which extends over the entire length L 25 (see FIG. 2).

Figure 3:
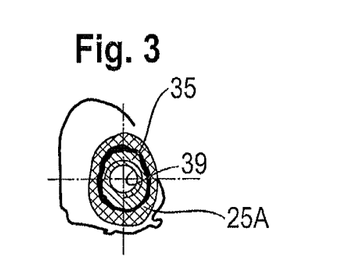
FIG. 3 shows the view of section in FIG. 2.
Figures 5, 6, 7A, 7B, 7C:
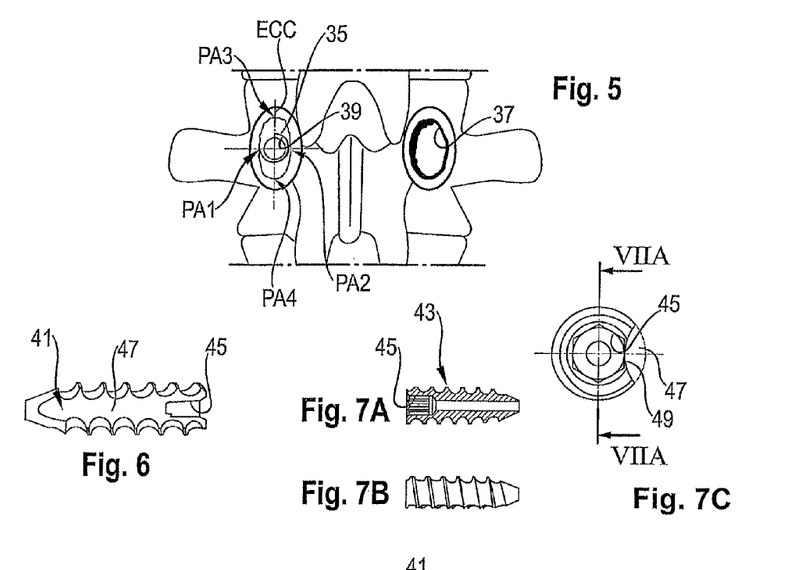
FIG. 5 shows the view of a vertebra with prepared pedicles for the insertion of a spacer according to the invention.
FIG. 6 shows the side view of a pedicle augmentation according to a further embodiment of the invention.
FIG. 7A shows an illustration drawn to scale of a longitudinal section of the pedicle augmentation according to FIG. 6.
FIG. 7B shows a side view of the pedicle augmentation according to FIG. 7A.
FIG. 7C shows in enlarged scale an end view of the pedicle augmentation according to FIG. 6.

Due to the structure of the pedicle cross section apparent from FIG. 1, there arises that the cylindrical body also has a cross-section deviating from the circular shape, namely an elliptical cross-section, which is shown in the illustrations according to FIGS. 3 and 5. In detail, the cylindrical body is received with a form-locking fit in a prepared—that means sunk in the pedicle 25—axial recess 37 which is shown in FIG. 5. The recess 37 is preferably milled into the vertebra with the aid of a drilling jig or another tool. Alternatively a preparation with help of an ultrasound osteotome is also possible. Preferably the outer surface of the spacer 35 is provided with a knurling or a microknurling, in order to improve the toothed engagement over the entire circumference with the inner surface of the recess 37.

An axial through-hole extends through the spacer 35, which in the shown example is a threaded hole 39 for the accommodation of the threaded portion 29 of the pedicle screw 27.

The spacer is for example made of plastic, preferably from a PEEK-plastic, because this material distinguishes itself through its particular biological compatibility and longevity with simultaneously high stiffness. In order to improve the long term connection between spacer and bone structure, it is advantageous to appropriately coat the spacer, for example to provide it with a porous titanium coating such as that offered by the Applicant Aesculap AG under the designation Plasmapore. Other materials may also be applied, such as for example titanium or a titanium alloy, synthetic bone substitutes or allogenic bone material. Furthermore collagen, a pressed textile structure or other lattice structures may be used, as are used in the area of implant technology and nowadays are manufacturable from plastic or a metallic material in any desired shape and with arbitrary lattice orientation and lattice dimensioning according to a 3-D printing process or according to a laser sintering process.

From the view in FIGS. 5 and 3 it becomes clear that, due to the anchoring according to the invention, of the pedicle screw, in addition to the group stabilization of the threaded portion via the support points PA1 and PA2 known from conventional solutions, according to the invention an additional support, not achieved until now, in the cranio-caudal direction, that is to say in the region of the plane ECC, i.e. in the region of the points PA3, PA4, is provided, whereby there results a type of all-round support of the pedicle screw at the cortical edge layer 25A of the pedicle 25. Transverse forces, in particular those that act in the cranio-caudal direction, and bending moments can in this way be accommodated significantly better than conventionally, such that the connection is reliably secured against loosening of the pedicle screw.

In the following a further embodiment of the invention is explained in more detail with reference to FIGS. 6 to 16.

In the case of the second embodiment the task of the spacer 35 described in the first embodiment assumes the role of an essentially cylindrical so-called pedicle augmentation 41 which is inserted axially parallel to the pedicle screw in the pedicle. The essentially cylindrical pedicle augmentation 41 essentially has the shape of a bone screw or bone dowel, i.e. it is provided on the outer side with an anchoring thread 43 and it has a polygonal recess on the screw head of the pedicle screw 127, that is to say at the proximal end face, which may be for example a hexagonal recess 45 for the corresponding screwing-in tool.

Figure 8:
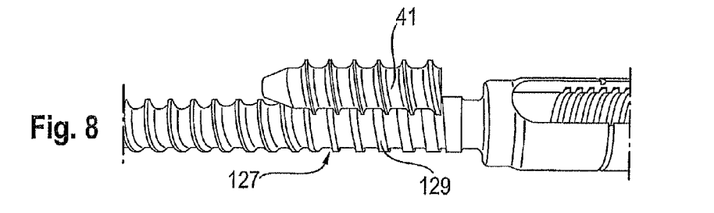
FIG. 8 shows a view for clarification of the positional assignment between pedicle screw and pedicle augmentation according to FIG. 6 in the assembled state.
Figure 9:
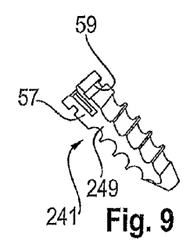
FIG. 9 shows a perspective representation of the pedicle augmentation according to FIG. 6.

As can be seen from the illustration according to FIG. 8, the essentially cylindrical pedicle augmentation 41 has a cylindrical recess 47 on the side facing the threaded portion 129, which cylindrical recess extends essentially over the entire length of the pedicle augmentation 41—as can be seen from FIG. 6. It can be recognized from the illustration according to FIG. 7C that the cross-section of the cylindrical recess 47 is essentially lens-like.

The shape of the cylindrical recess 47 is selected such that it coincides with the envelope of the threaded portion 129 of the pedicle screw 127. In other words in the inserted state of the pedicle augmentation 41 and pedicle screw 127, the threaded portion 129 clings to the inner wall of the cylindrical recess 47. In this way the threaded portion 129, upon screwing in at the pedicle augmentation 41, can support with radial clamping.

The pedicle augmentation 41 and pedicle screw 127 are fitted such that the cancellous bone in the pedicle 25 is filled as completely as possible by these two components. In other words the pedicle screw is positioned more cranially or caudally than in the case of the embodiment according to FIGS. 1 to 6, such that the pedicle screw can support in the cranial or caudal area of the pedicle over several points at the periphery on the cortical layer of the pedicle cross-section. The threaded portion 129 can also obtain a support on the other side of the pedicle screw via the cylindrical recess 47 with the support surface 49, under interconnection of the pedicle augmentation 41 on the other side of the pedicle screw, such that again a type of all-round support of the threaded portion 129 at the corticalis of the pedicle 25 is provided.

There occurs in addition a fixing of both components in the axially parallel orientation via the support surface 49 of the cylindrical recess 47. For the implantation, auxiliary apparatuses are used in order to set the exact axial distance between pedicle screw 127 and pedicle augmentation 41. The planning of the positioning can thereby take place for example intra-operatively via a conventional x-ray. Particularly preferably the components are introduced with the help of a navigation system.

An exemplary insertion is done whereby first the augmentation 41 is set, wherein the required hole is center-punched, then a pilot drilling and possibly a thread cutting is performed. As soon as the augmentation 41 is set, the drilling device can come into operation for the drilling of the pedicle screw 127. The drilling device in this case advantageously supports itself at the augmentation 41 via a so-called K-wire and thus prescribes the drilled hole for the pedicle screw 127. The screwing-in of the pedicle screw 127 takes place once more via a positioned K-wire.

It can be seen best from the illustration according to FIG. 8 that upon screwing in of the pedicle screw 127, the threaded portion 129 is in constant contact with the support surface 49 of the pedicle augmentation 41. By means of appropriate configuring of the support surface 49 to suit the surface enveloping the threaded portion 129, the radial clamping between the threaded portion 129 and pedicle augmentation 41 can be controlled in the desired manner.

In the configuration shown according to FIGS. 6 to 8, the support surface 49 is configured to be smooth so that no toothed engagement takes place with the screw threads of the threaded portion 129. In a modification of the embodiment shown, a profiling may however additionally be introduced in this region, with which it is possible to provide also for an additional axial clamping between the threaded portion 129 and pedicle augmentation 41, in the region of the support surface 49.

In the following there are described exemplary embodiments of the system according to the invention, for the anchoring of a pedicle screw in a vertebra, with which there is ensured a fixed connection between the pedicle screw on the one side and the augmentation on the other side. In describing these variants, similar reference signs are used for those components which correspond to the elements of the previously described embodiment examples, to which a '2' (FIGS. 9 to 16), '3' (FIGS. 17 to 19) or '4' (FIGS. 20 to 22) is prefixed.

In the embodiment according to FIGS. 9 to 16, pedicle screw and pedicle augmentation are connected via a connection plate 51 through which the pedicle augmentation 241 and the pedicle screw 227 extend on one side. The pedicle augmentation 241 is—with the exception of the augmentation head—configured in the same way as the pedicle augmentation 41 of the embodiment according to FIGS. 6 to 8, that means it again has an essentially crescent-shaped cross-section which occurs by means of the cylindrical recess 247. The region 247 cut out from the cross-section of the pedicle augmentation 241 is best inferable from FIG. 12.

For the form-locking accommodation of pedicle augmentation 241 and pedicle screw 227, two axially parallel axial breakthroughs 53 and 55 are formed in the connection plate 51, wherein in the shown embodiment these axial breakthroughs are formed by circular-cylindrical intersecting breakthroughs. The breakthrough 53 serves the purpose of the accommodation of a circular-cylindrical head section 57 of the pedicle augmentation 241, which—as with the embodiment according to FIGS. 6 to 8—is provided with an inner polygonal recess 245. The head section 57 bears on the outer side an annular segment groove indicated with 59, in which a securing projection 61 can engage with a form-locking fit, which securing projection 61 projects from the inner surface of the breakthrough 53 of the connection plate 51.

Figures 10, 11, 12:
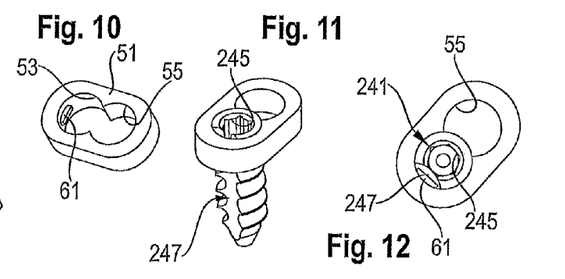
FIG. 10 shows a perspective view of a connection plate between a pedicle augmentation according to FIG. 6 and a pedicle screw to be used in conjunction with it.
FIG. 11 shows a perspective view of the assembly between pedicle augmentation and connection plate in the pre-assembled state.
FIG. 12 shows the top view of the assembly according to FIG. 11.
Figure 13A:
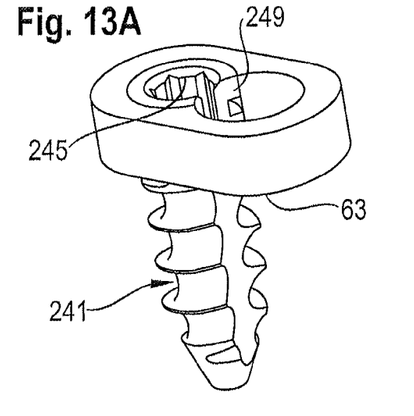
FIG. 13A and FIG. 13B show in enlarged representation the assembly of pedicle augmentation and connection plate in the ready assembled state before the screwing-in of the pedicle screw.
Figure 13B:
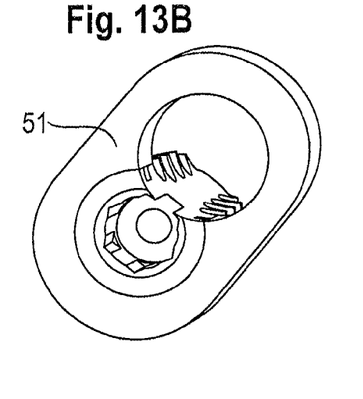
Figure 16:
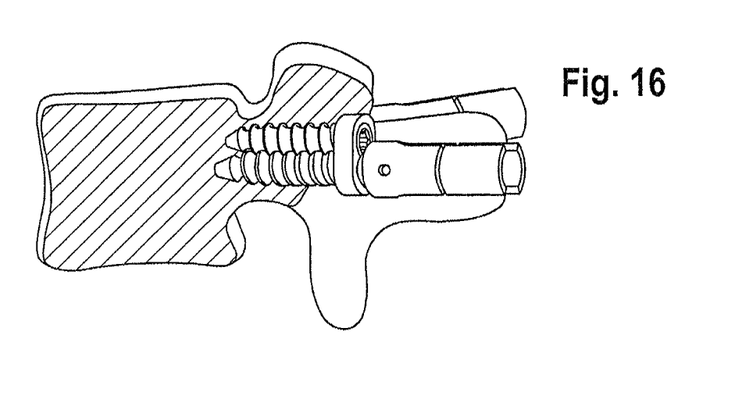
FIG. 16 shows a longitudinal section through the vertebra with inserted pedicle screw and pedicle augmentation according to the invention.

The securing projection 61 has—as can be best seen from FIG. 12—a surface protruding from the inner surface, which is smaller than the lens shaped cross-section (see FIG. 12) of the recess 247 in the pedicle augmentation 241. Due to this design a free axial movement between pedicle augmentation 241 and connection plate 51 is provided, as long as the securing projection 61 does not submerge in the annular segment groove 59 of the head section 57 of the pedicle augmentation 41. Upon assembly one proceeds by screwing the augmentation 241 so far into a correspondingly prepared hole or threaded hole that when placing the connection plate 51 in the position shown in FIG. 12, with a further turning of the pedicle augmentation 241 and therefore an accompanying axial offset of the pedicle augmentation, the securing projection 61 can submerge in the annular segment groove 59 and can still be turned by approximately 180°, until the pedicle augmentation 241 reaches the position shown in FIG. 13A and FIG. 13B, in which position the support surface 249 completes the circular segment of the circular-cylindrical breakthrough 55 into a full circle and the bottom-side surface 63 of the connection plate 51 is in firm contact with the vertebral bone. In this position, shown in FIGS. 13A and 13B, the positioning or screwing-in of the pedicle screw 227 can begin. The pedicle screw 227 can be guided via the circular-cylindrical breakthrough 55 and in the last assembly steps can be fixed in the exact axial distance to the pedicle augmentation 241, which is shown in FIGS. 14 to 16.

Figure 14A:
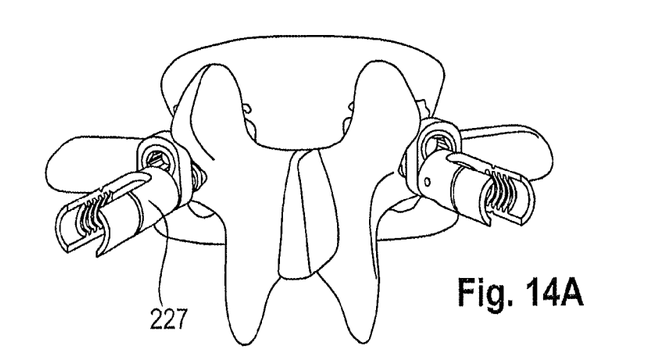
FIG. 14A and FIG. 14B show different views of a vertebra having pedicle screws assembled on both sides and pedicle augmentation according to the invention.
Figure 14B:
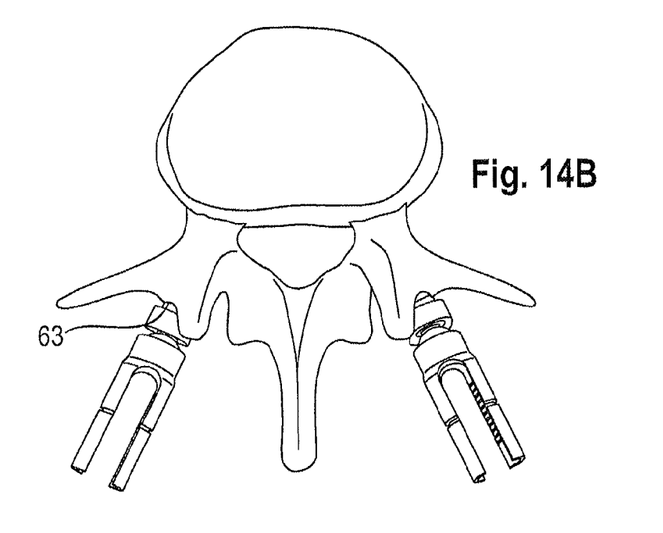
Figure 15A:
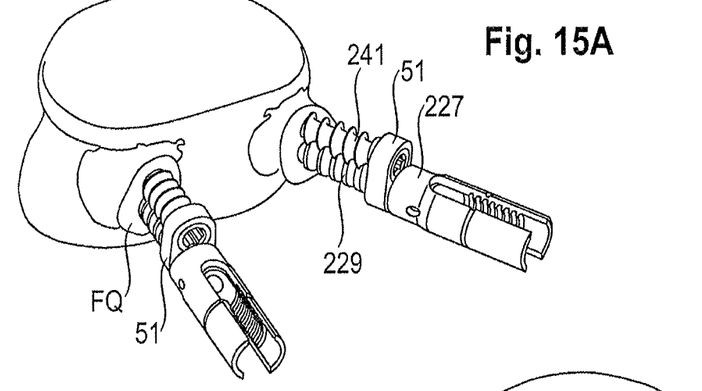
FIG. 15A and FIG. 15B show views of a vertebra having pedicle screws assembled on both sides and pedicle augmentation according to the invention for the case of a truncated vertebral arch.
Figure 15B:
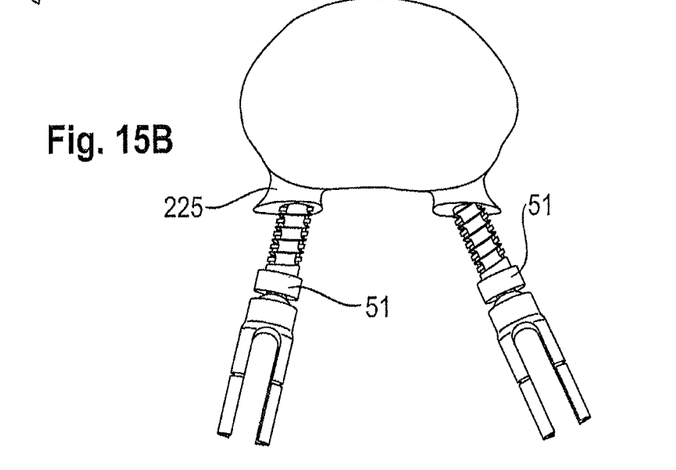

It can be recognized from the illustrations according to FIGS. 14A and 14B that the pedicle augmentation 241 is locked with the connection plate 51 in the position in which the latter is located in firm contact with an end face 63 of the vertebral arch. However, it should be emphasized at this point that a fixed contact with such an end face is not necessarily required. The decisive factor is much more that—as is apparent from the sectional views of FIGS. 15A and 15B, as well as from the illustration in FIG. 16—the threaded portion 229 of the pedicle screw 227 and the connected cross-section of the pedicle augmentation 241 fill up the cross-section FQ of the pedicle 225 so far that more or less the entire cancellous bone is filled up by these cross-sections and the pedicle screw 227 or the threaded portion 229 of the pedicle screw 227 can support itself all around at the corticalis of the pedicle 225.

The embodiments of FIGS. 6 to 16 described above are constructed such that the pedicle screw cooperates with a single pedicle augmentation 41 or 241, in order to ensure the effect according to the invention of anchoring the pedicle screw in the pedicle. It is however equally possible to execute the pedicle screw augmentation with the aid of several augmentations.

Figure 17:
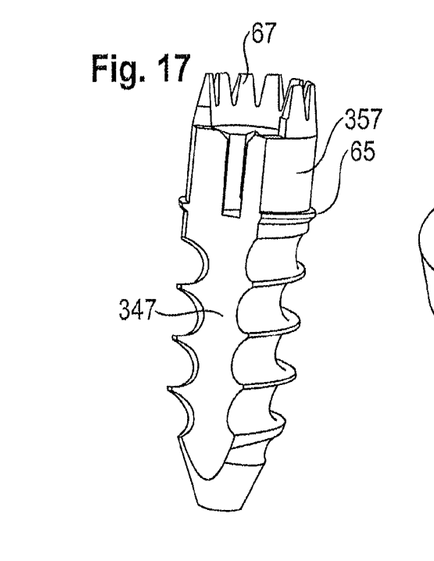
FIG. 17 shows in enlarged representation a variant of the pedicle augmentation.
Figure 18:
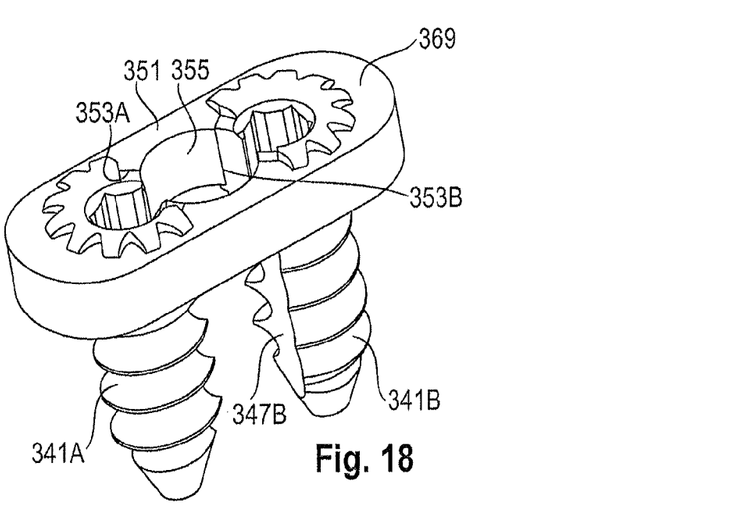
FIG. 18 shows an assembly of a modified embodiment of the pedicle augmentation with assembled connection plate according to a further embodiment.
Figure 19A:
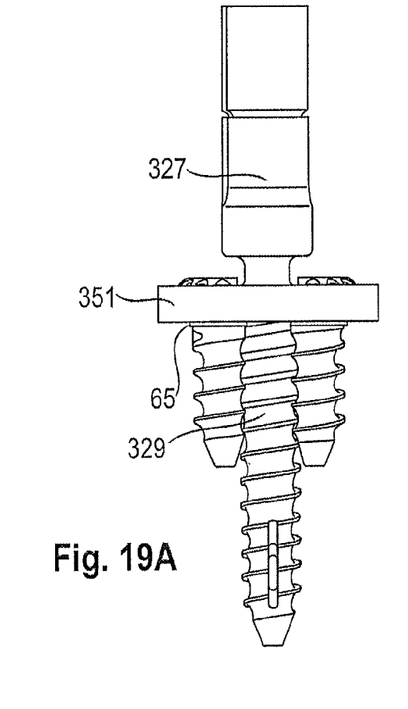
FIG. 19A and FIG. 19B show different representations of the pedicle augmentation according to FIG. 18 and an inserted pedicle screw.
Figure 19B:
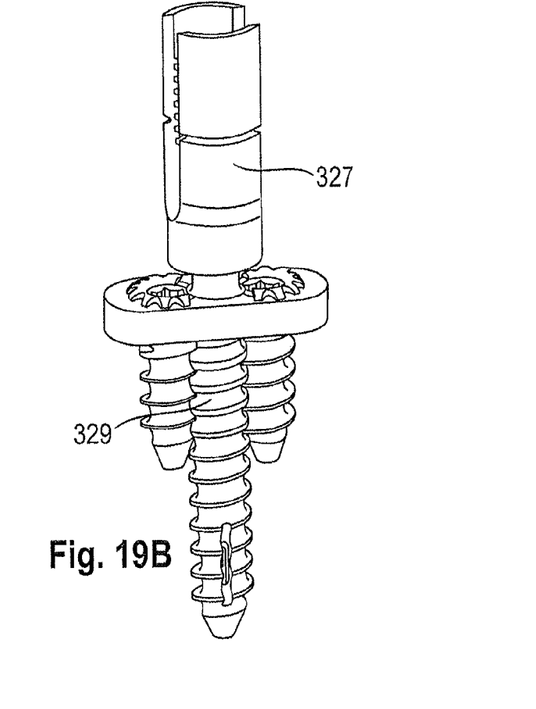

An embodiment is described in FIGS. 17 to 19 whereby the two pedicle augmentations 341A and 341B are set cranially or caudally with respect to the pedicle screw 327. For the fixing of the axial distance between pedicle augmentation 341A, B and threaded portion 329 of the pedicle screw 327, a connection plate 351 is provided in which there are configured three circular-cylindrical coaxial breakthroughs 353A, B for the head section 357 of the pedicle augmentations 341A, B and a central circular-cylindrical breakthrough 355 the pedicle screw 327.

The axial fixing between pedicle augmentation 341A, B and connection plate 351 takes place in the case of the embodiment according to FIGS. 17 to 19 whereby the head section 357 under support of an annular shoulder of the head section 357 is caulked with the connection plate 351. To this aim, the head section 357 bears a ring of tongue-like protrusions 67 which can be bent and pushed into the upper end face 369 for the purpose of caulking, as shown in FIG. 18.

Also in the embodiment according to FIGS. 17 to 19, the insertion of the pedicle screw can take place such that the connection plate 351 bears on the bone substance. In this case it is advantageous to provide at least the area of the connection plate 351 which comes into contact with the bone substance with an appropriate coating in order to allow bone growth.

Figure 20:
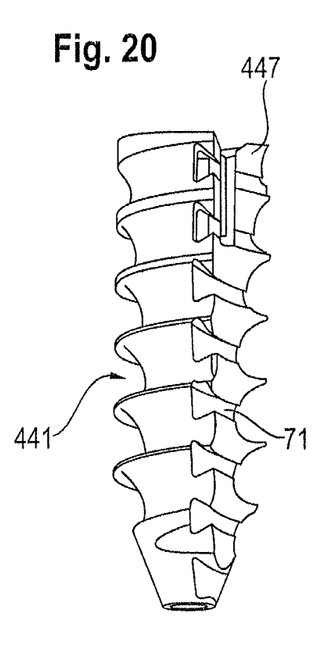
FIG. 20 shows a perspective view of a further embodiment of a pedicle augmentation according to the invention.
Figure 21:
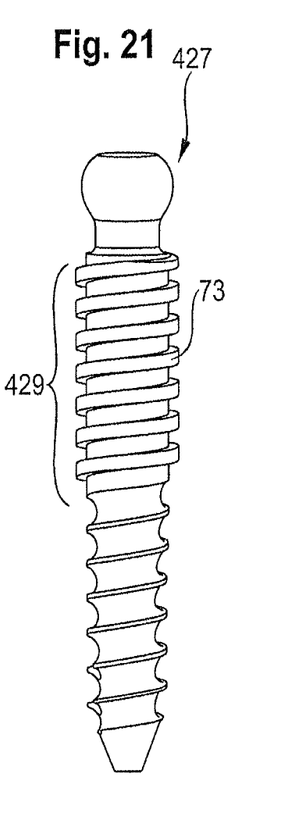
FIG. 21 shows a side view of an associated pedicle screw.
Figure 22:
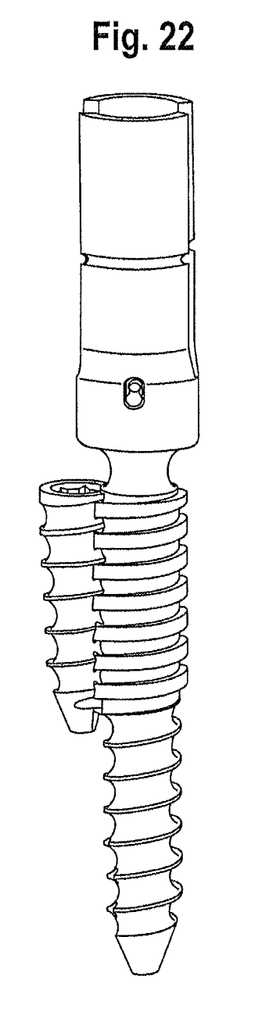
FIG. 22 shows a schematic view of the assembly of the pedicle augmentation according to FIG. 20 and pedicle screw according to FIG. 21.

As an alternative to the above described positional fixing between pedicle augmentation and pedicle screw in the form of the connection plate 51/351, or additionally to this positional fixing, an alternative is described in the following with reference to FIGS. 20 to 22. This consists of providing the pedicle augmentation indicated with the reference sign 441 in the region of its cylindrical recess 447 with an undercut thread 71 which is configured complementarily to a modified screw thread 73 in the threaded portion 429 of the pedicle screw 427. The scales of the illustrations of FIGS. 20 to 22 are different. It is self-explanatory that the threaded portion 429 has an axial length which matches the axial length of the undercut thread 71 in the region of the pedicle augmentation 441.

With this design it is possible, when the pedicle augmentation 441 is set, to screw in the pedicle screw 427 (which in the configuration according to FIGS. 21 and 22 is a polyaxial pedicle screw) into the prepared and exactly placed pilot hole of the pedicle such that after a predetermined screw-in extent, the thread length of the screw thread 73 engages in the undercut thread segments of the undercut thread 71. The two components are coupled together by means of the undercut of the thread. The arrangement may even be provided that the two complementary threaded portions are biased with respect to one another. This arrangement makes it possible to do without a connection plate 51 or 351.

The pedicle augmentation according to the invention described above is configured such that it can be made without a cementation with so-called bone cement, i.e. polymeric methyl methacrylate (PMMA). It is however possible to achieve the pedicle augmentation with the aid of cement augmentation screws. Such a pedicle screw is shown in FIG. 19A and FIG. 19B with the reference sign 329. With such a screw there occurs a conventional cementation only in the vertebral body, while in the pedicle channel exclusively the pedicle augmentation described above is applied. Thereby there results the particular advantage that no risk of an uncontrolled cement leakage arises.

With the pedicle augmentation described above it is also effectively excluded that there arises a local destruction of the pedicle structure. The risk of an over-stressing of the pedicle structure can additionally be reduced in that a suitable preparation of the vertebra is performed.

Of course deviations from the shown embodiments are possible without departing from the principle of the invention. As an alternative to the embodiments of FIGS. 9 to 19 more augmentations may be used which for example are placed in a star-shape. It is also possible by use of two or more pedicle augmentations to use different cross-sections, when thereby an even better filling of the cancellous bone of the pedicle is achieved. Of course for the individual components of the pedicle augmentation all materials used so far in the area of Orthopaedic Technology may be applied.

Alternatively to the accommodation of the head section 57 or 357 of the pedicle augmentation 241, 341, a conical head section or a stepped head section may also be used. It is also possible to axially shorten the pedicle augmentation such that it reaches around only a predetermined shortened longitudinal section of the pedicle channel.

The invention thus provides a system for anchoring a pedicle screw in a vertebra of a patient, in particular in the lumbar or thoracic region of the spinal column. The system has a pedicle screw which comprises a threaded portion sinkable in the vertebral arch including the pedicle. The space between the threaded portion and cortical edge layer of the pedicle is filled at least in regions by a spacer which is configured or positioned with respect to the threaded portion in the pedicle cross section such that an all-round support of the threaded portion at the cortical edge layer via the spacer is enabled. The invention furthermore provides a corresponding kit for the system wherein the kit consists of a standard pedicle screw and a spacer which at least in regions fills the space between the threaded portion and cortical edge layer of the pedicle. Finally, the invention provides a corresponding spacer in the form of a cylindrical body having an essentially oval cross-section for form-locking fit in a corresponding axial recess sunk in the pedicle and having an axial through-hole for the accommodation of the threaded portion of a pedicle screw, as well as a spacer in the form of an essentially cylindrical pedicle augmentation which has the form of a bone screw or a bone bracket and has a cylindrical recess on one side for the radial support of a threaded portion of a pedicle screw.

The invention claimed is:

1. A system for anchoring a pedicle screw in a vertebra of a patient, the system comprising:
    a pedicle screw having a threaded portion sinkable in the vertebral arch including the pedicle, comprising at least one spacer filling at least in regions the space between the threaded portion and cortical edge layer of the pedicle, the spacer being configured or positioned with respect to the threaded portion in the pedicle cross section such that an all-round support of the threaded portion at the cortical edge layer via the at least one spacer is enabled,
    wherein the at least one spacer is formed from an essentially cylindrical pedicle augmentation axially parallel to the pedicle screw inserted in the vertebra, which pedicle augmentation has essentially the shape of a bone screw or a bone dowel and has a cylindrical recess on the side facing the pedicle screw on which the threaded portion supports itself with radial clamping, and
    wherein the at least one pedicle augmentation and the pedicle screw extend through a common connection plate in which axial breakthroughs are configured for the form-locking accommodation of a head section of the pedicle augmentation and a guide portion of the pedicle screw, said guide portion lying beneath the screw head.

2. The system of claim 1, wherein the spacer is composed of plastic including PEEK plastic, and comprises a porous titanium coating.

3. The system of claim 1, wherein the spacer is formed of one or more of titanium, titanium alloy, synthetic bone substitutes, allogenic bone material, collagen, pressed textile material or any lattice structure material.

4. The system of claim 1, wherein the threaded portion supports itself at the pedicle augmentation additionally with axial clamping.

5. The system of claim 1, wherein the axial breakthroughs are formed from circular-cylindrical intersecting breakthroughs.

6. The system of claim 1, wherein the connection plate serves for the axial fixing of the pedicle augmentation and as an axial stop for the pedicle screw.

7. The system of claim 6, wherein the axial breakthrough for the pedicle augmentation bears, on the side facing away from the breakthrough for the pedicle screw, a securing projection which is receivable with form-locking fit in an annular segment groove of the head section of the pedicle augmentation.

8. The system of claim 7, wherein the securing projection has a surface radially protruding from the inner wall, which surface is smaller than the cross-section of the cylindrical recess in the pedicle augmentation.

9. The system of claim 6, wherein the at least one pedicle augmentation is caulkable with the connection plate.

10. The system of claim 1, wherein the cylindrical recess in the pedicle augmentation is provided with a thread which can be brought into operative engagement with the threaded portion of the pedicle screw.

11. The system of claim 10, wherein the thread in the pedicle augmentation is undercut.

12. The system of claim 1, wherein the pedicle augmentation and/or the connection plate is composed of a titanium alloy and comprises at least in regions a porous titanium coating.

13. A kit for a system for anchoring a pedicle screw in a vertebra of a patient, the kit comprising a pedicle screw having a threaded portion sinkable in the vertebral arch including the pedicle, comprising at least one spacer filling at least in regions of the space between the threaded portion and cortical edge layer of the pedicle, the spacer being configured or positioned with respect to the threaded portion in the pedicle cross section such that an all-round support of the threaded portion at the cortical edge layer via the at least one spacer is enabled, the kit further comprising a connection plate in which axial breakthroughs are configured for the form-locking accommodation of a head section of a pedicle augmentation and a guide portion of the pedicle screw, said guide portion lying beneath a screw head portion of the pedicle screw.

* * * * *